United States Patent [19]
Dolisi

[11] Patent Number: 5,989,567
[45] Date of Patent: Nov. 23, 1999

[54] METHOD AND DEVICE FOR INFANT MALE CIRCUMCISION ANESTHESIA

[76] Inventor: Frank Dolisi, 21 Woodland Rd., Old Brookville, N.Y. 11545

[21] Appl. No.: 09/016,189

[22] Filed: Jan. 30, 1998

Related U.S. Application Data

[60] Provisional application No. 60/070,108, Dec. 31, 1997.

[51] Int. Cl.⁶ .................................................. A61B 17/326
[52] U.S. Cl. ......................... 424/400; 606/118; 606/141; 427/2.3
[58] Field of Search .............................. 427/2.3; 606/118, 606/141; 424/400

[56] References Cited

U.S. PATENT DOCUMENTS

| | | |
|---|---|---|
| 4,840,188 | 6/1989 | Heidenfelder . |
| 5,704,906 | 1/1998 | Fox . |

*Primary Examiner*—Thurman K. Page
*Assistant Examiner*—Brian K. Seidleck
*Attorney, Agent, or Firm*—Alfred M. Walker

[57] ABSTRACT

A device which produces adequate local anesthesia for the purpose of infant male circumcision. The elastic form fitting body of the device is measured to fit over the infant male penis, and contains a coated inner surface that contacts the penile skin with an anesthetic gel, which upon contact, initiates anesthesia locally at the glans tip of the infant penis.

14 Claims, 2 Drawing Sheets

Fig. 4
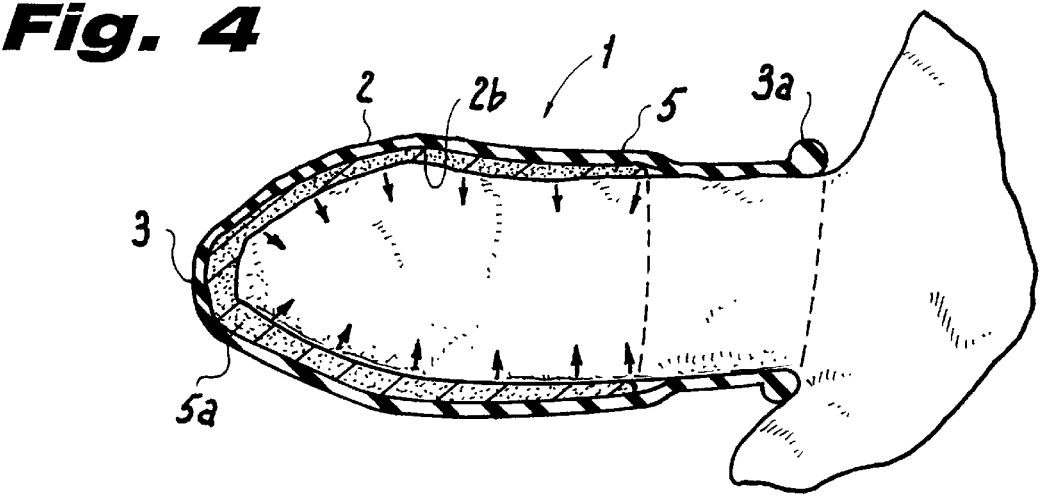
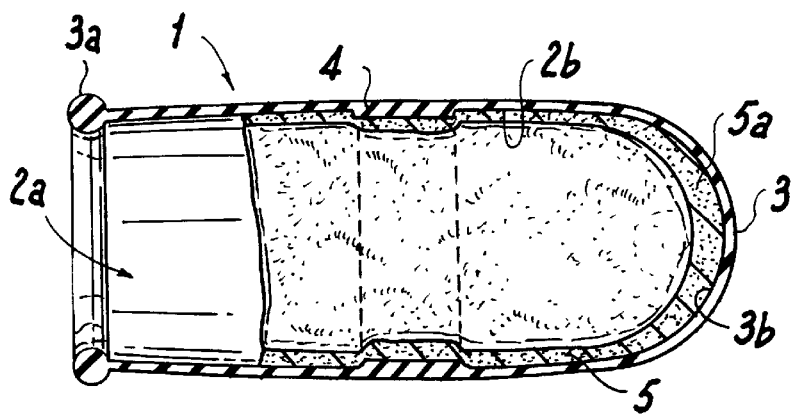
Fig. 5
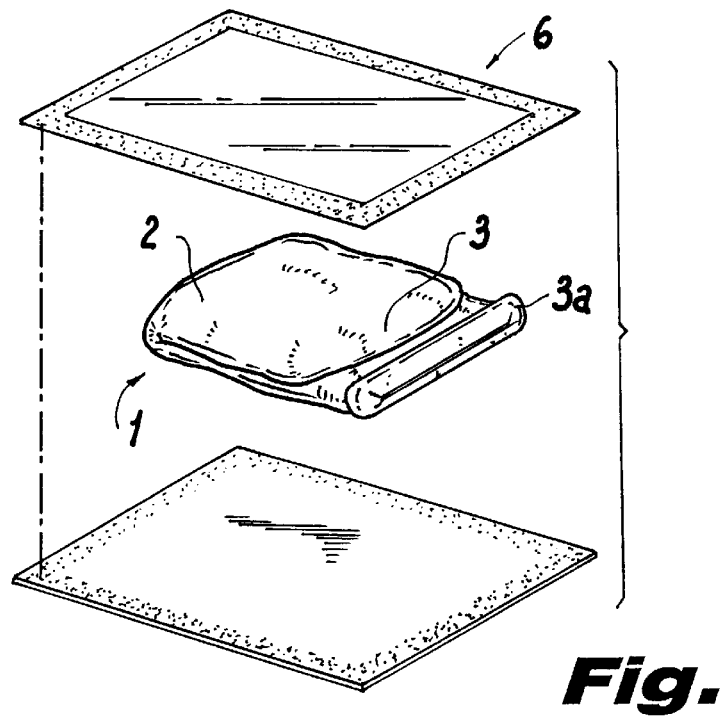
Fig. 6

METHOD AND DEVICE FOR INFANT MALE CIRCUMCISION ANESTHESIA

RELATION TO RELATED APPLICATIONS

This application is based upon my provisional application No. 60/070,108 filed on Dec. 31, 1997.

FIELD OF THE INVENTION

This invention relates to devices and methods for producing adequate anesthesia in order to perform infant male circumcision.

BACKGROUND OF THE INVENTION

The process of male circumcision in the infant is accomplished using several different surgical techniques. Although this operation is very common and is often performed within the first 24 hours of life, there is often no anesthetic used during the procedure. Recent evidence suggests that the experience is in fact painful for the infant and the operation would be better performed using anesthesia.

The present methods of anesthesia, not including general anesthesia, include the application of a local anesthetic such as LIDOCAINE® via injection into the penis or via the application of a gel which is then wrapped with a sheet-like gauze material to hold the gel in place prior to the start of the procedure. These two common methods are not without flaws. The injection of anesthetic can cause complications such as pain, bleeding, hematoma and cardiac arrest if accidentally injected into the vascular tree. The application of anesthesia locally with a wrap is less dangerous but is more cumbersome to carry out. This method is time consuming and requires two procedures. This makes the method more difficult to perform and less cost effective. If the anesthetic is absorbed by the sheet-like material used to wrap around the penis to hold it in place, it will also take longer for the penis to become adequately anesthetized. This will therefore decrease the use of the anesthetic in performing circumcisions.

It is therefore desirable to provide a method and device for providing adequate anesthesia for the operation of infant male circumcision which does not require injection or cumbersome, time consuming and special skill requiring use.

OBJECTS OF THE INVENTION

Among the several objects of the invention may be noted the provision of a novel device for administering anesthesia in order to perform infant male circumcision.

It is also an object to provide a device for maintaining local anesthesia adequately for the time necessary to perform the circumcision procedure.

It is yet another object to provide a novel infant male circumcision anesthetic device having an interior surface coated with an anesthetic.

It is also an object to provide a method for applying and maintaining adequate anesthesia for the procedure of infant male circumcision.

Other objects of this invention may be in part apparent from the following description of the invention, or will in fact be pointed out hereinafter.

SUMMARY OF THE INVENTION

The present invention describes an anesthetic-coated device, such as a pediatric condom-shaped body, which is coated on its interior surface with a common topical anesthetic such as LIDOCAINE®.

While the anesthetic coating extends within the condom-shaped body, preferably the anesthetic is placed especially at the closed end of the device and along the interior surface, but not at the open end of the condom, for the first 5–10 millimeters from the open end. The closed end and the upper 20 millimeters is the most important area wherein the foreskin comes into the most contact with the anesthetic. In order to accomplish this, the device can also be optionally fitted with a narrow constricting elastic rim at or near the mid portion of the device.

The device produces adequate local anesthesia for the purpose of infant male circumcision. The elastic condom-shaped form fitting body of the device is measured to fit over the infant male penis, and contains a coated inner surface that contacts the penile skin with an anesthetic, such as a gel, which upon contact, initiates anesthesia locally, at the glans tip of the infant penis.

Generally, the device is similar in shape to an adult condom, but is modified in length and width to conform to the pediatric patient's penis. Further modifications include a change in the shape of the device to allow a narrower constricting portion midway through the length of the device.

Between the closed end portion and the open end portion, there is applied a coating of anesthetic gel throughout the inner lining thereof, but the coating is especially concentrated at the closed end portion thereof.

The anesthetic most typically used is LIDOCAINE® gel but other agents can be used such as EMLA®, produced by Astra Pharmaceuticals which is a combination of LIDOCAINE® and PRILOCAINE® anesthetics. The device can further be utilized to deliver other types of medications, such as antiseptics for the infant penis and/or to provide pressure for hemostasis at a surgical site on the infant penis.

Prior to the start of the procedure, the condom is fitted onto the infant's penis. The anesthetic, placed in the proper portions of the condom-shaped body, then comes into direct contact with the penile skin. This contact results in gradual anesthesia. This effect allows the surgeon to perform the operation with diminished pain to the patient.

The invention is comprised of the construction and methods which will now be described and the scope of the invention is indicated in the following claims.

BRIEF DESCRIPTION OF THE DRAWINGS

The present invention can best be understood in connection with the accompanying drawings, in which:

FIG. 4 is a cross-sectional side view of the infant male circumcision anesthesia device as in FIG. 2, shown in place upon a penis of an infant male;

FIG. 5 is a cross sectional side view of an alternate embodiment for an infant male circumcision anesthesia deliver device, with a constricted annular band reinforcing rib therein, and FIG. 6 is an exploded isometric view of the infant male circumcision anesthesia device as in FIG. 2, shown folded within a sealed package container.

DETAILED DESCRIPTION OF THE INVENTION

Figure 1:
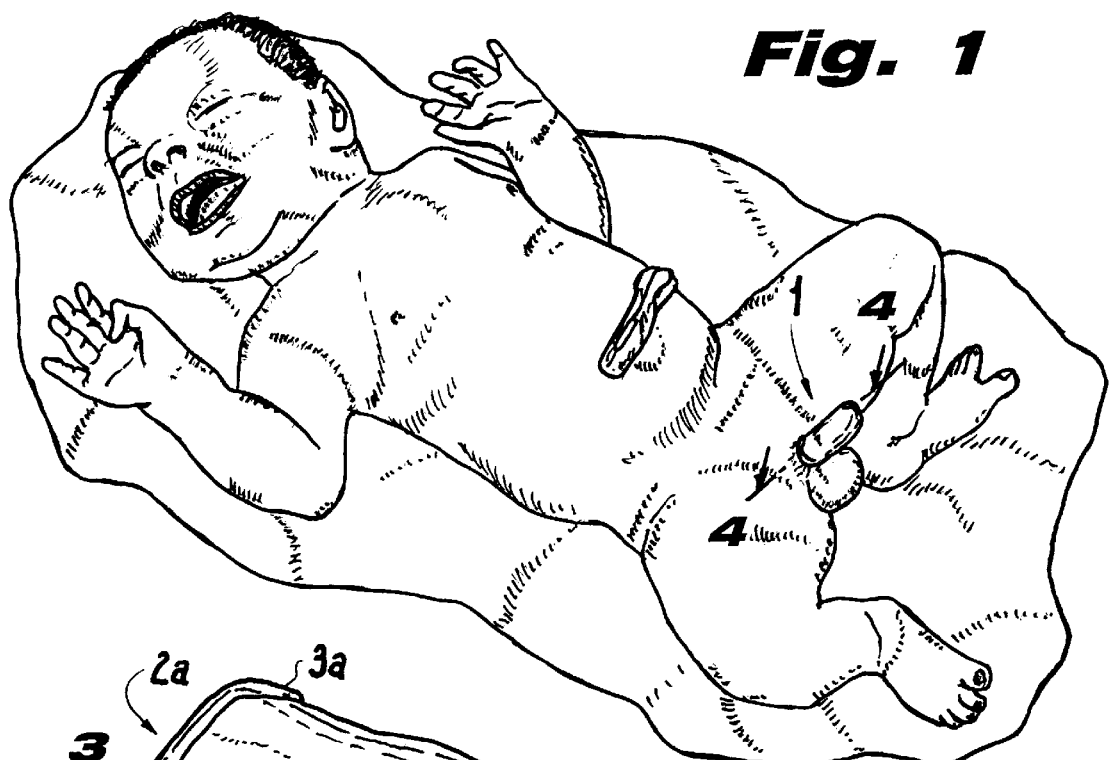
FIG. 1 is a perspective view of an infant male shown with the circumcision anesthesia delivery device of the present invention in place.
Figure 2:
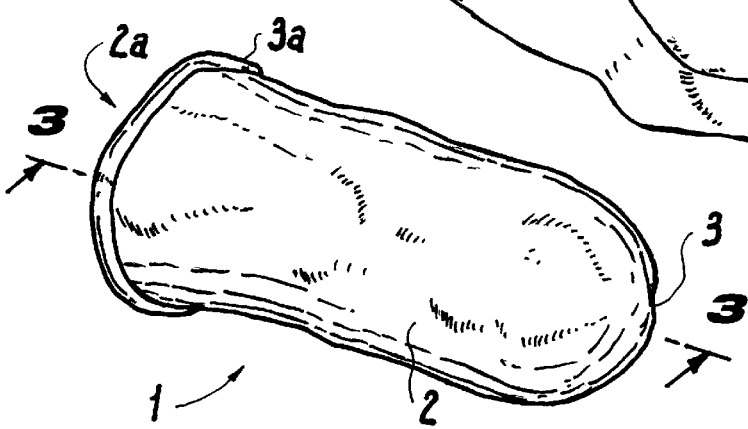
FIG. 2 is an isometric side view of the infant male circumcision anesthetic delivery device of the present invention.

Circumcision anesthesia delivery device 1 includes hollow miniature condom-shaped body 2 and anesthetic coating 5 therein. Condom shaped body 2 has closed distal end 3, open rimmed proximal end 3a and hollow longitudinally extending interior cavity 2a having anesthetic coating 5 therein.

Figure 3:
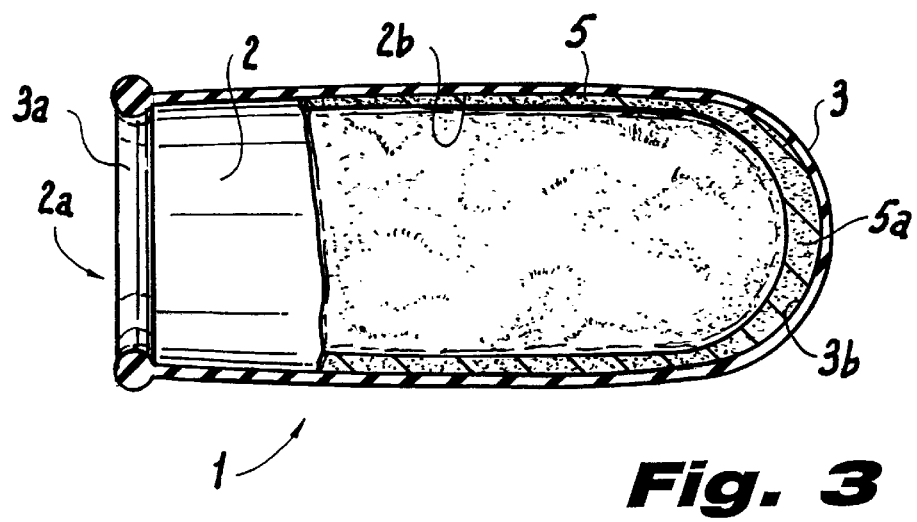
FIG. 3 is a cross-sectional end view of the infant male circumcision anesthesia device as in FIG. 2, taken along lines 3—3 of FIG. 2.

Device 1 can be generally seen as described in the side view in cross section of FIG. 3, which shows device 1 including a miniature elastic form fitting condom shaped body 2 or modified version thereof, which condom shaped body 2 also includes rimmed open end, portion 3a, and closed end portion 3.

It is known that condom-shaped body 2 can be made of latex or other suitable flexible materials such as vinyl or polypropylene. Gel coating 5 is placed substantially throughout the axial length of inner surface 2b of body 2 of device 1 but is especially concentrated at end coating 5a, located at closed end portion 3b of inner surface 2b, superior to the constricted area. This can best be seen in cross sectional view of FIG. 3.

As shown in FIG. 4, to anesthetize the infant male's penis, inner surface 2b of condom shaped body 2 of device 1 is coated with coating 5 of a topical anesthetic, such as the commonly used LIDOCAINE® gel, forming an inner lining of said coating, which coating 5 is transdermally migrated through the skin and tissues of the infant male's penis, in the directions of the arrows shown in FIG. 4.

Optionally, at a region which is located approximately longitudinally midway through condom-shaped body 2 of device 1, thickened narrower constricting band 4 can be placed, as shown in FIG. 5. This insures that most of the anesthetic gel controls the glans tip region of the infant's penis.

In using device 1, the infant male penis is fitted within miniature modified pediatric condom body 2 of device 1, by the steps of first unfolding condom shaped body of device 1, then grasping open rim 3a, and inserting the penis into interior 2a of hollow condom-shaped body 2 of device 1.

Condom shaped body 2 of device 1 is preferably placed along the full length of the infant male's penis, with care taken to assure that the glans tip of the penis and its surrounding foreskin are in contact with the superior closed end portion 3b of inner surface 2b, of condom shaped body 2 of device 1, where a concentrated amount 5a of anesthetic coating 5 is located.

As shown in FIG. 6, once anesthetic coating 5 is applied to inner surface 2b of condom shaped body 2, the modified miniature pediatric condom body 2 of device 1 can be packaged in a suitable airtight package wrapper 6, such as a foil wrapper, that is already known and used with adult prophylactic devices.

Also shown in FIG. 6, since device 1 is a special apparatus that is not typically packaged for pediatric use, condom body 2 device 1 should not be rolled as a typical adult condom in wrapper 6. Instead both the small size of condom body 2 of device 1 and the application of the anesthetic coating 5, which coating 5 is concentrated in the coating portion 5a at closed end 3 thereof, require condom-body 2 of device 1 to be preferably folded in half before being placed in the wrapper 6.

There are many advantages that can be seen from the above description of the invention. Device 1, including condom shaped body 2 and anesthetic coating 5 therein, allows for a superior method of achieving anesthesia for the purpose of infant male circumcision. Unlike the conventional prior art anesthetic procedures, device 1 of the present invention allows for the safe, simple, and effective application of topical anesthetic, such as coating 5.

Device 1 does not carry the risks of anesthetic injection, nor does device 1 require special techniques used conventionally in preparing for circumcisions, such as separately applying an anesthetic gel to a male infant penis, and then using a special wrapping to hold the anesthetic gel in place for up to 30 minutes before the circumcision procedure. It is also a more effective delivery system because the anesthetic is not be absorbed by condom body 2.

Furthermore, if an anesthetic is simply placed on the penis without a device to keep it in place, the anesthetic is be easily washed or rubbed off as the infant moves and therefore produces inadequate anesthetic effects to the foreskin of the penis.

In view of the aforementioned, it will be seen that the many objects of the invention are achieved and other results that are advantageous attained. For example, a user may take an empty miniature condom, similar to condom-shaped body 2 of device 1, and apply an appropriate amount of coating of an anesthetic into the condom shaped body just before use, by spraying, pouring or other like application.

As it is possible for changes to be made in the above constructions without departing from the scope of the invention, it is intended that the above description and accompanying drawings should be interpreted as illustrative in a general sense, and not in a limiting capacity.

I claim:

1. A method of anesthetizing an infant penis prior to circumcision comprising the steps of coating the inside of a condom sized to fit the infant penis with sufficient anesthetic to anesthetize the foreskin of the penis for surgical circumcision and for a distance from the closed end to make contact with the full length of the foreskin, folding said condom in a location to confine said anesthetic to said distance, unfolding said condom just prior to use and inserting the infant penis in said condom.

2. The method as in claim 1, further comprising the step of providing means for controlling with said anesthetic the glans tip region of the penis, said means comprising an annular band portion extending around said condom at a region located midway through a predetermined longitudinal length of said condom.

3. The method as claimed in claim 1, wherein said coating extends about 20 millimeters inside said condom from a region located about 5 to 10 millimeters from the open end.

4. The method as in claim 1, wherein said anesthetic is a gel.

5. The method as in claim 1, wherein said anesthetic is a lotion.

6. The method as in claim 1, wherein said anesthetic is a solution.

7. The method as in claim 1, wherein said anesthetic is a mixture.

8. A method of anesthetizing an infant penis prior to circumcision comprising the steps of applying, just before use, to the inside of a condom sized to fit the infant penis a predetermined quantity of sufficient anesthetic to anesthetize the foreskin of the penis for surgical circumcision and for a distance from the closed end to make contact with the full length of the foreskin, and inserting the infant penis in said condom.

9. The method as in claim 8, further comprising the step of providing means for controlling with said anesthetic the glans tip region of the penis, said means comprising an annular band portion extending around said condom at a region located midway through a predetermined longitudinal length of said condom.

10. The method as claimed in claim 8, wherein said coating extends about 20 millimeters inside said condom from a region located about 5 to 10 millimeters from the open end.

11. The method as in claim 8, wherein said anesthetic is a gel.

12. The method as in claim 8, wherein said anesthetic is a lotion.

13. The method as in claim 8, wherein said anesthetic is a solution.

14. The method as in claim 8, wherein said anesthetic is a mixture.

\* \* \* \* \*